(12) United States Patent
Bryant

(10) Patent No.: US 7,772,156 B2
(45) Date of Patent: Aug. 10, 2010

(54) MICROBICIDAL COMPOSITIONS INCLUDING A CYANODITHIOCARBIMATE AND A SECOND MICROBICIDE, AND METHODS OF USING THE SAME

(75) Inventor: Stephen D. Bryant, Bartlett, TN (US)

(73) Assignee: Buckman Laboratories International, Inc., Memphis, TN (US)

( * ) Notice: Subject to any disclaimer, the term of this patent is extended or adjusted under 35 U.S.C. 154(b) by 465 days.

(21) Appl. No.: 11/555,301

(22) Filed: Nov. 1, 2006

(65) Prior Publication Data

US 2008/0102094 A1    May 1, 2008

(51) Int. Cl.
| | |
|---|---|
| A01N 59/24 | (2006.01) |
| A01N 43/80 | (2006.01) |
| A01N 43/00 | (2006.01) |
| A01N 47/00 | (2006.01) |
| A01N 37/52 | (2006.01) |
| A01N 47/40 | (2006.01) |
| A01N 37/06 | (2006.01) |
| A01N 33/02 | (2006.01) |
| A01N 35/04 | (2006.01) |
| A01N 41/10 | (2006.01) |
| A01N 33/14 | (2006.01) |
| A01N 31/08 | (2006.01) |

(52) U.S. Cl. .................. 504/118; 504/141; 504/143; 504/148; 504/150; 504/154; 504/157; 504/161; 514/231.2; 514/367; 514/372; 514/383; 514/479; 514/508; 514/515; 514/547; 514/642; 514/689; 514/709; 514/727; 514/731

(58) Field of Classification Search .............. 424/405, 424/404; 504/118, 141, 143, 148, 150, 154, 504/157, 158, 161; 514/231.2, 367, 372, 514/383, 479, 508, 515, 547, 642, 689, 709, 514/727, 731
See application file for complete search history.

(56) References Cited

U.S. PATENT DOCUMENTS

| | | | |
|---|---|---|---|
| 2,881,070 A | 4/1958 | Pera | |
| 2,840,598 A | 6/1958 | Schwartz | |
| 3,193,448 A | 7/1965 | Buckman et al. | |
| 3,299,129 A | 1/1967 | D'Amico | |
| 3,520,976 A | 7/1970 | Buckman et al. | |
| 3,524,871 A | 8/1970 | Matt | |
| 3,923,870 A | 12/1975 | Singer | |
| 3,952,002 A | 4/1976 | Kramer et al. | |
| 3,959,328 A | 5/1976 | Buckman et al. | |
| 4,079,062 A | 3/1978 | Van Reet et al. | |
| 4,124,637 A | 11/1978 | Gutman | |
| 4,293,559 A | 10/1981 | Buckman et al. | |
| 4,479,961 A | 10/1984 | Martin | |
| 4,510,136 A | 4/1985 | Moberg | |
| 4,532,341 A | 7/1985 | Holmwood et al. | |
| 4,551,469 A | 11/1985 | Parry et al. | |
| 4,595,691 A | 6/1986 | LaMarre et al. | |
| 4,652,580 A | 3/1987 | Janssen et al. | |
| 4,664,696 A | 5/1987 | Schaub | |
| 4,839,373 A | 6/1989 | Ito et al. | |
| 4,866,081 A | 9/1989 | Ito et al. | |
| 4,944,892 A | 7/1990 | Leathers et al. | |
| 4,945,109 A | 7/1990 | Rayudu | |
| 5,073,638 A | 12/1991 | Conaway et al. | |
| 5,087,635 A | 2/1992 | Shaber | |
| 5,200,421 A | 4/1993 | Ludwig et al. | |
| 5,219,875 A | 6/1993 | Sherba et al. | |
| 5,250,194 A | 10/1993 | Hollis et al. | |
| 5,250,559 A | 10/1993 | Mittermeier et al. | |
| 5,266,585 A | 11/1993 | Hubele et al. | |
| 5,326,777 A | 7/1994 | Ludwig et al. | |
| 5,328,926 A | 7/1994 | Oppong | |
| 5,403,844 A | 4/1995 | Mittermeier et al. | |
| 5,413,795 A | 5/1995 | Lee et al. | |
| 5,444,078 A | 8/1995 | Yu et al. | |
| 5,567,705 A | 10/1996 | Mittermeier et al. | |
| 5,571,443 A * | 11/1996 | Dalton et al. | ............... 252/8.57 |
| 5,627,135 A | 5/1997 | Gartner | |
| 5,627,188 A | 5/1997 | Mittermeier et al. | |
| 7,157,017 B2 | 1/2007 | Fenyes et al. | |
| 2005/0109975 A1 * | 5/2005 | Fenyes et al. | ............... 252/8.57 |

FOREIGN PATENT DOCUMENTS

| | | |
|---|---|---|
| DE | 241204 A1 | 12/1986 |
| DE | 275 433 A1 | 1/1990 |
| DE | 275391 A1 | 1/1990 |
| GB | 2 119 653 A | 11/1983 |
| WO | WO 96/25044 | 8/1996 |

OTHER PUBLICATIONS

International Search Report and Written Opinion of the International Searching Authority for corresponding International Patent Application No. PCT/US2007/082798 dated Jan. 29, 2009 (15 pages).

* cited by examiner

Primary Examiner—John Pak
Assistant Examiner—Andriae M Holt
(74) Attorney, Agent, or Firm—Kilyk & Bowersox, P.L.L.C.

(57) ABSTRACT

Microbicidal compositions including (a) cyanodithiocarbimate and (b) an N-alkyl heterocyclic compound; a triazole compound or salt thereof or metal complex thereof; a microbicide with an activated halogen atom or a formaldehyde releasing compound; 1,4-bis(bromoacetoxy)-2-butene; 2-(thiocyanomethylthio)benzothiazole; a methylene-bis (thiocyanate); a halogenated acetophenone; a halopropynl compound; an iodosulfone; a phenol; a halocyanoacetamide compound and/or a quaternary ammonium compound are described. Components (a) and (b) can be present in a synergistically effective amount to control the growth of at least one microorganism. Methods for controlling the growth of microorganisms with the compositions are also disclosed.

25 Claims, No Drawings

MICROBICIDAL COMPOSITIONS INCLUDING A CYANODITHIOCARBIMATE AND A SECOND MICROBICIDE, AND METHODS OF USING THE SAME

BACKGROUND OF THE INVENTION

The present invention relates to compositions and methods for controlling the growth of microorganisms on a variety of mediums, substrates and in aqueous systems. More particularly, the invention relates to a combination of cyanodithiocarbimates with one or more microbicides.

Many industrial materials and media when wet or subjected to treatment in water are susceptible to bacterial, fungal, and/or algal deterioration or degradation. A large variety of commercial, industrial, agricultural, and wood materials or products are subject to microbiological attack or degradation which reduces or destroys their economic value. These industrial materials and media include, but are not limited to, for example, wood pulp, wood chips, lumber, adhesives, coatings, animal hides, paper mill liquors, pharmaceutical formulations, cosmetic formulations, toiletry formulations, geological drilling lubricants, petrochemicals, agrochemical compositions, paints, leathers, plastics, seeds, plants, wood, metalworking fluids, cooling water, recreational water, influent plant water, waste water, pasteurizers, retort cookers, tanning liquors or solutions, starch, proteinaceous materials, acrylic latex paint emulsions, and textiles. The various temperatures at which such materials or products are manufactured, stored, or used as well as their intrinsic characteristics make them susceptible to growth, attack, and degradation by common microorganisms such as algae, fungi, yeasts, and bacteria. These microorganisms may be introduced during a manufacturing or other industrial process, by exposure to air, tanks, pipes, equipment, and humans. They can also be introduced while using a material or product, for example, by multiple openings and reclosures of packages or from stirring or removing material with contaminated objects.

To control deterioration or degradation caused by microorganisms, various industrial microbicides are used. Workers in the trade have continued to seek improved biocides that have low toxicity, are cost effective, and are also capable of exhibiting a prolonged biocidal effect against a wide variety of microorganisms with regular use.

Aqueous systems are also highly subject to microbiological growth, attack, and degradation. These aqueous systems may be fresh, brackish or saltwater systems. Exemplary aqueous systems include, but are not limited to, latexes, surfactants, dispersants, stabilizers, thickeners, adhesives, starches, waxes, proteins, emulsifying agents, cellulose products, metal working fluids, cooling water, waste water, aqueous emulsions, aqueous detergents, coating compositions, paint compositions, and resins formulated in aqueous solutions, emulsions or suspensions. These systems frequently contain relatively large amounts of water and organic material causing them to be environments well-suited for microbiological growth and thus attack and degradation.

Microbiological degradation of aqueous systems may manifest itself as a variety of problems, such as loss of viscosity, gas formation, objectionable odors, decreased pH, emulsion breaking, color change, and gelling. Additionally, microbiological deterioration of aqueous systems can cause fouling of the related water-handling system, which may include cooling towers, pumps, heat exchangers, and pipelines, beating systems, scrubbing systems, and other similar systems.

Another objectionable phenomenon occurring in aqueous systems, particularly in aqueous industrial process fluids, is slime formation. Slime formation can occur in fresh, brackish or salt water systems. Slime consists of matted deposits of microorganisms, fibers and debris. It may be stringy, pasty, rubbery, tapioca-like, or hard, and may have a characteristic undesirable odor that is different from that of the aqueous system in which it formed. The microorganisms involved in its formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeast, and yeast-like organisms. Slime reduces yields in production and causes plugging, bulking, and other problems in industrial water systems.

Despite the existence of such microbicides, industry is constantly seeking more cost-effective technology which offers equal or better protection at lower cost and lower concentration. The concentration of conventional microbicides and the corresponding treatment costs for such use, can be relatively high. Important factors in the search for cost-effective microbicides include the duration of microbicidal effect, the ease of use and the effectiveness of the microbicide per unit weight.

SUMMARY OF THE INVENTION

It is a feature of this invention to provide a microbicidal composition capable of controlling the growth of at least one microorganism, for example, fungi, bacteria, algae, or mixtures thereof, for example, over short or over prolonged periods of time. It is an additional feature of this invention to provide such compositions which are economical to use. Methods of controlling the growth of at least one microorganism are also features of this invention.

Compositions and processes useful for controlling the growth of one or more microorganisms are described. Compositions and methods for preventing damage during storage caused by microorganisms, such as bacteria, fungi, algae, or mixtures thereof, are described.

The present invention, in part, relates to a composition and more particularly, a microbicidal composition or formulation.

The present invention provides a composition comprising a) a cyanodithiocarbimate and b) a second microbicide selected from an N-alkyl heterocyclic compound; a triazole compound or salt thereof or metal complex thereof; a microbicide with an activated halogen atom or a formaldehyde releasing compound; 1,4-bis(bromoacetoxy)-2-butene; 2-(thiocyanomethylthio)benzothiazole; a methylene-bis (thiocyanate); a halogenated acetophenone; a halopropynl compound; an iodosulfone; a phenol; a halocyanoacetamide compound; a quaternary ammonium compound; or any combination thereof, where components a) and b) are present in a combined amount synergistically effective to control the growth of at least one microorganism.

The present invention provides a method for controlling the growth of at least one microorganism in or on a product, material, or medium susceptible to attack by the microorganism. This method includes the step of adding to the product, material, or medium a composition of the present invention in an amount synergistically effective to control the growth of the microorganism. The synergistically effective amount varies in accordance with the product, material, or medium to be treated and can, for a particular application, be routinely determined by one skilled in the art in view of the disclosure provided herein.

The present invention also embodies the separate addition of the cyanodithiocarbimate and the second microbicide to products, materials, or media. According to this embodiment, the components are individually added to the products, materials, or media so that the final amount of each component present at the time of use is that amount synergistically effective to control the growth of at least one microorganism.

The compositions of the present invention are useful in preserving or controlling the growth of at least one microorganism in various types of industrial products, media, or materials susceptible to attack by microorganisms. Such media or materials include, but are not limited to, for example, dyes, pastes, lumber, leathers, textiles, pulp, wood chips, tanning liquor, paper mill liquor, polymer emulsions, paints, paper and other coating and sizing agents, metalworking fluids, geological drilling lubricants, petrochemicals, cooling water systems, recreational water, influent plant water, waste water, pasteurizers, retort cookers, pharmaceutical formulations, cosmetic formulations, and toiletry formulations.

The composition can also be useful in agrochemical formulations for the purpose of protecting seeds or crops against microbial spoilage.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

It is understood that both the foregoing general description and the following detailed description are exemplary and explanatory only, and are not restrictive of the present invention as claimed.

DETAILED DESCRIPTION OF CERTAIN EMBODIMENTS

The present invention provides a composition to control the growth of at least one microorganism comprising a mixture (or a formulation) of a) at least one cyanodithiocarbimate and b) at least a second microbicide selected from an N-alkyl heterocyclic compound; a triazole compound or salt thereof or metal complex thereof; a microbicide with an activated halogen atom or a formaldehyde releasing compound; 1,4-bis(bromoacetoxy)-2-butene; 2-(thiocyanomethylthio)benzothiazole; a methylene-bis(thiocyanate); a halogenated acetophenone; a halopropynl compound; an iodosulfone; a phenol; a halocyanoacetamide compound; a quaternary ammonium compound; or any combination thereof, wherein the cyanodithiocarbimate and the second microbicide can be present in a combined amount synergistically effective to control the growth of at least one microorganism. The composition can provide superior microbicidal activity at low concentrations or other concentrations against a wide range of microorganisms.

The compositions of the present invention can be used in a method for controlling the growth of at least one microorganism in or on a product, material, or medium susceptible to attack by the microorganism. This method includes the step of adding to the product, material, or medium a composition of the present invention, where the components of the composition can be present in synergistically effective amounts to control the growth of the microorganism.

The synergistically effective amount varies in accordance with the material or medium to be treated and can, for a particular application, be routinely determined by one skilled in the art in view of this disclosure.

In lieu of adding the composition of the present invention to a material or medium to be treated, the cyanodithiocarbimate and the second microbicide can be separately added to the material or medium to be treated. These components are individually added so that the final amount of the mixture of cyanodithiocarbimate and the second microbicide at the time of use can be that amount synergistically effective to control the growth of at least one microorganism.

As stated earlier, the compositions of the present invention are useful in preserving various type of industrial products, media, or materials susceptible to attack by at least one microorganism. The compositions of the present invention are also useful in agrochemical formulations for the purpose of protecting seeds or crops against microbial spoilage. These methods of preserving and protecting are accomplished by adding the composition of the present invention to the products, media, or materials in an amount that can be synergistically effective to preserve the products, media, or materials from attack by at least one microorganism or to effectively protect the seeds or crops against microbial spoilage.

According to the methods of the present invention, controlling or inhibiting the growth of at least one microorganism includes the reduction and/or the prevention of such growth.

It is to be further understood that by "controlling" (i.e., preventing) the growth of at least one of microorganism, the growth of the microorganism is inhibited. In other words, there is no growth or essentially no growth of the microorganism. "Controlling" the growth of at least one microorganism maintains the microorganism population at a desired level, reduces the population to a desired level (even to undetectable limits, e.g., zero population), and/or inhibits the growth of the microorganism. Thus, in one embodiment of the present invention, the products, material, or media susceptible to attack by the at least one microorganism are preserved from this attack and the resulting spoilage and other detrimental effects caused by the microorganism. Further, it is also to be understood that "controlling" the growth of at least one microorganism also includes biostatically reducing and/or maintaining a low level of at least one microorganism such that the attack by the microorganism and any resulting spoilage or other detrimental effects are mitigated, i.e., the microorganism growth rate or microorganism attack rate is slowed down and/or eliminated.

When two chemical microbicides are mixed and added to the product, or added separately, three results are possible:

1) The chemicals in the product would produce an additive (neutral) effect.

2) The chemicals in the product would produce an antagonistic effect, or

3) The chemicals in the product would produce a synergistic effect.

An additive effect has no economic advantage over the individual components. The antagonistic effect would produce a negative impact. Only a synergistic effect, which is less likely than either an additive or antagonistic effect, would produce a positive effect and therefore possess economic advantages.

It is known in the microbicidal literature that there is no theoretical method to anticipate additive, antagonistic, or synergistic effects when two biocides are mixed to yield a new formulation. Nor is there a method to predict the relative proportions of the different biocides required to produce one of the three effects described above.

Thus, these compositions preferably achieve superior, i.e. greater than additive, microbicidal activity, even at low concentrations, against a wide variety of microorganisms. Examples of these microorganisms include fungi, bacteria, algae, and mixtures thereof such as, but not limited to, for example, *Trichoderma viride, Aspergillus niger, Pseudomonas aeruginosa, Klebsiella pneumoniae*, and *Chlorella* sp. The compositions of the present invention can have a low toxicity.

The cyanodithiocarbimates can be of formula (I)

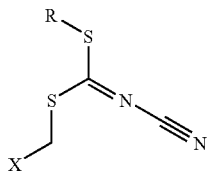

Mixtures of cyanodithiocarbimates of formula (I) may also be used.

In formula (I), X is a halogen, preferably Cl, Br, or I. Most preferably X is Cl.

The substituent R may be a substituted or unsubstituted $C_1$-$C_{14}$ alkyl group, a substituted or unsubstituted $C_2$-$C_{14}$ alkenyl group, or a substituted or unsubstituted $C_2$-$C_{14}$ alkynyl group. The substituent R may also be a substituted or unsubstituted group defined by Y—Ar—$(CH_2)_m$— or by Z—$(CH_2)_m$—. In the Y—Ar—$(CH_2)_n$— group, m ranges from 0 to 3. Ar is a substituted or unsubstituted aryl group selected from phenyl and naphthyl. Y is H, halogen, $NO_2$, $R^1$, $R^{10}$, or $R^1R^2N$. When R is the group defined by Z—$(CH_2)_n$—, Z is NC, $R^{10}$, $R^{10}C(O)$, or $R^{10}CR_2CH_2(OCH_2CH_2)_p$ where p ranges from 0 to 3. The value of n ranges from 0 to 3. $R^1$ and $R^2$ are independently H, substituted or unsubstituted $C_1$-$C_5$ alkyl.

In a preferred embodiment, R is a substituted or unsubstituted $C_1$-$C_7$ alkyl group, a substituted or unsubstituted $C_2$-$C_7$ alkenyl group, a substituted or unsubstituted group defined by Y—Ar—$(CH_2)_m$— or by Z—$(CH_2)_n$—. The value of n ranges from 0 to 3. In the Y—Ar—$(CH_2)_m$— group, m is 0 or 1. Ar is preferably phenyl. Y is H, Cl, Br, I, $NO_2$, $R^1$, $R^{10}$, or $R^1R^2N$. When R is the group defined by Z—$(CH_2)_n$—, wherein Z is NC, $R^{10}$, $R^{10}C(O)$, or $R^{10}CH_2CH_2(OCH_2CH_2)_p$ where p ranges from 0 to 3. $R^1$ and $R^2$ are independently H, methyl, or ethyl. Preferred cyanodithiocarbimates are shown below in Table 1.

As further examples, with reference to the above formula, X is a halogen; R is a substituted or unsubstituted $C_4$-$C_{14}$ alkyl group, a substituted or unsubstituted $C_2$-$C_{14}$ alkenyl group with the proviso that it is not —$CH_2CH=CH_2$, a substituted or unsubstituted $C_2$-$C_{14}$ alkynyl group, a substituted or unsubstituted group defined by Y—Ar—$(CH_2)_m$— or by Z—$(CH_2)_n$—; Ar is a substituted or unsubstituted aryl group selected from phenyl, and naphthyl;

Y is H, halogen, $NO_2$, $R^1$, $R^{10}$, $R^1R^2N$;

Z is NC, $R^{10}$, $R^{10}C(O)$, $R^{10}CH_2CH_2(OCH_2—CH_2)_p$ m is 0, 2, or 3;

n ranges from 0 to 3;

p ranges from 0 to 3; and $R^1$ and $R^2$ are independently H, substituted or unsubstituted $C_1$-$C_5$ alkyl.

Preferred cyanodithiocarbimates of formula (I) are those where:

R is a substituted or unsubstituted $C_5$-$C_7$ alkyl group, a substituted or unsubstituted $C_2$-$C_7$ alkenyl group with the proviso that it is not —$CH_2CH=CH_2$, a substituted or unsubstituted group defined by Y—Ar—$(CH_2)_m$— or by Z—$(CH_2)_n$—;

Ar is phenyl;

Y is H, Cl, Br, I, $NO_2$, $R^1$, $R^{10}$, or $R^1R^2N$;

Z is NC, $R^{10}$, $R^{10}C(O)$, or $R^{10}CH_2CH_2(OCH_2CH_2)_p$ m is 0; and $R^1$ and $R^2$ are independently H, methyl, or ethyl.

More preferred cyanodithiocarbimates of formula (I) are those where:

X is Cl and R is -iso-pentyl, —$(CH_2)_5CH_3$, —$(CH_2)_7CH_3$, —$(CH_2)_{11}CH_3$ —$CH(CH_3)_2$, —$CH(CH_3)(CH_2)_3CH_3$, —$(CH_2)_2OH$, —$(CH_2)_3OH$, —$(CH_2CH_2O)_2CH_2CH_2OH$, —$(CH_2)_2CO_2H$, —$CH_2CH_2CN$, or —$CH_2C_6H_5$;

X is Br and R is —$(CH_2)_3CH_3$, or —$CH_2C_6H_5$; or

X is I and R is —$(CH_2)_3CH_3$, or $CH_2C_6H_5$.

A particularly preferred cyanodithiocarbimates of formula (I) is hexyl chloromethyl cyanodithiocarbimate.

For cyanodithiocarbimates of formula (I) the alkyl, alkenyl, or alkynyl groups may be branched or unbranched (i.e., a straight chain). An alkenyl or alkynyl group may be unsaturated at more than one position and may contain both carbon-carbon double bonds and carbon-carbon triple bonds. As indicated various groups may be substituted or unsubstituted by one or more groups that do not adversely effect the microbicidal activity of the cyanodithiocarbimate. Unsubstituted means the particular moiety carries hydrogen atoms on its constituent atoms, e.g. $CH_3$ for unsubstituted methyl. Substituted means that the group can carry typical functional groups know in organic chemistry. Such functional groups include, but are not limited to, halides, hydroxyl, thiols, amine groups, carboxylic acid groups, ketones, aldehydes, nitrites, nitro, azo, nitroso, ethers, thioethers, amides, and the like.

TABLE 1

Preferred Cyanodithiocarbimates

| |
|---|
| X is Cl |
| R is iso-pentyl, —$CH_3$, —$(CH_2)_2CH_3$, —$(CH_2)_3CH_3$, —$(CH_2)_5CH_3$, —$(CH_2)_7CH_3$, —$(CH_2)_{11}CH_3$, —$CH(CH_3)_2$, —$CH(CH_3)(CH_2)_3CH_3$, —$(CH_2)_2OH$, —$(CH_2)_3OH$, —$(CH_2CH_2O)_2CH_2CH_2OH$, —$(CH_2)_2CO_2$—H, —$CH_2CH_2CN$, —$CH_2CH=CH_2$, $CH_2C_6H_5$ |
| X is Br |
| R is —$(CH_2)_3CH_3$, —$CH_2C_6H_5$ |
| X is I |
| R is —$(CH_2)_3CH_3$, —$CH_2C_6H_5$. |

The cyanodithiocarbimates used in the present invention may be the same as and prepared according to U.S. Patent Application Publication No. 2005/0109975, incorporated by reference herein. Starting materials to prepare other preferred cyanodithiocarbimates include, for example, hexyl chloride, ethyl bromide, propyl bromide, isopropyl bromide, butyl bromide, hexyl bromide, 2-hexyl bromide, octyl bromide, dodecyl bromide, allyl bromide, methyl iodide, hexyl iodide, 3-bromo-1-propanol, chloroethanol, chloroethoxyethoxyethanol, bromopropionic acid, benzyl bromide, 4-methyl benzyl bromide, 4-Chlorobenzyl bromide, and bromopropionitrile. Published synthetic methods for cyanodithiocarbimates such as ethyl chloromethyl cyanodithiocarbimate, propyl chloromethyl cyanodithioicarbimate, isopropyl chloromethyl cyanodithiocarbimate, allyl chloromethyl cyanodithiocarbimate, and benzyl chloromethyl cyanodithiocarbimate are reported in C. Fieseler, W. Walek and U. Thust, Tag.-Ber. Akad. Landwirtsch.-Wiss. DDR, Berlin (1990) 291. 317-321; and German Patent DD 275433 CYANOIMIDODITHIOCARBONATES AS WOOD PRESERVATIVES to W. Walek, J. Nauman, H. D. Pfeiffer, U. Thust, K. Trautner, C. Fieseler, M. Heschel, R. Hesse, H. Kirk and D. Mielke.

The effective amount to be present with a second microbicide(s) can be readily determined by one skilled in the art. For a particular application, the amount of choice may be determined by routine testing of various amounts prior to treatment of the substrate or system. In general, an effective amount used on a substrate or medium ranges from about 0.0001% to about 4% (w/w); preferably about 0.0001% to about 0.2%. With aqueous systems, an effective amount may range from about 5 to about 1000 parts per million of the aqueous system, preferably from, about 10 to about 500 parts per million, and more preferably be about 300 parts per million.

In the methods of the invention, the cyanodithiocarbimates of formula (I) may be formulated in various forms known in the art. For example, they may be prepared in liquid form as an aqueous solution, dispersion, emulsion, or suspension, a dispersion or suspension in a non-aqueous solvent, or as a solution by dissolving the compound(s) to be used in a solvent or combination of solvents. Suitable solvents include, but are not limited to, methyl ethers of glycols, M-pyrol, or petroleum distillates. Diluents such as vegetable products including oils from: soybeans, pine trees, cottonseed, corn, canola, peanut, palm, rice, olive, tung nut, castor bean, linseed, citrus or datenut. The cyanodithiocarbimates may be prepared as a concentrate for dilution prior to its intended use. Common additives such as surfactants, emulsifiers, dispersants, and the like may be used as known in the art to increase solubility in a liquid composition or system, such as an aqueous composition or system. In many cases, the cyanodithiocarbimate compound(s) used may be solubilized by simple agitation.

Compositions containing a cyanodithiocarbimate to be used in the present invention may also be formulated in solid form, for example as a powder or tablet, using means known in the art. A liquid form can be deposited on a carrier such as diatomaceous earth, zeolites, kaolin, or a water-soluble salt matrix to form a powder or tablet.

With regard to the second microbicides, the N-alkyl heterocyclic compound that can be used in the present invention can have the following formula:

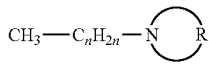

The variable "n" may vary from 5 to 17, and preferably from 7 to 15. Most preferably, n is 7 or 11. The alkyl chain defined by $CH_3C_nH_{2n}$— may be branched or unbranched. Branched alkyl chains may lose some of their solubility in water or other aqueous systems. Unbranched alkyl groups are generally preferred.

The heterocyclic ring defined by

may have four to eight members and is preferably a five-, six-, seven-, or eight-membered ring. Most preferably the heterocyclic ring is a six-membered ring. Although the heterocyclic ring always contains one nitrogen atom, the remainder is generally a carbocycle. However, the ring may contain one or more additional heteroatoms selected from N, O, or S. The ring may be saturated or unsaturated. The ring may also have common substituents such as alkyl groups, substituted alkyl groups, alkenyl groups, substituted alkenyl groups, amino groups, an oxo group to form a carbonyl group, halogens, and the like. The heterocyclic ring may also be part of a multiple ring structure.

The heterocycles listed below exemplify substituted or unsubstituted heterocyclic rings which may be used in the N-alkyl heterocyclic compounds utilized in preferred embodiments of the invention. Examples of five-membered heterocyclic rings include, but are not limited to, pyrrolidinyl, 2-pyrrolidinonyl, pyrrolinyl, pyrazolidinyl, pyrazolinyl, pyrazolyl, imidazolidinyl, imidazolinyl, imidazolyl and oxazolidinyl. Six-membered rings include, but are not limited to, piperidinyl, piperazinyl, and morpholinyl. Seven- and eight-membered rings such as hexamethyleneiminyl and heptamethyleneiminyl may also be used in the invention. One of ordinary skill will appreciate that other heterocyclic rings may also be used.

Salts of N-alkyl heterocyclic compounds, including those described above, may also be used in the present invention. Such salts are formed at the nitrogen moiety of the N-alkyl heterocyclic compound (referred to as "quaternized N-alkyl heterocyclic salts") and have the general formula

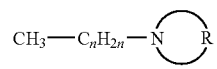

where n and

are as defined above. Preferably, the salts of the N-alkyl heterocyclic compounds are acid salts such as, for example, $C_1$-$C_{10}$ carboxylic acid salts. More preferably, the salt of the N-alkyl heterocyclic compound is a formic acid salt.

N-alkyl heterocyclic compounds or salts thereof useful in the invention are available either commercially from chemical supply houses or may be prepared from starting materials using well-known literature methods. U.S. Pat. No. 5,250,194 discloses exemplary methods and is incorporated herein by reference.

U.S. Pat. No. 5,250,194 also describes N-dodecyl heterocyclic compounds and their use as microbicides for aqueous systems to inhibit the growth of microorganisms, the formation of slime in aqueous systems, or the disfigurement or deterioration of substances susceptible to microbiological growth. One example of an N-alkyl heterocyclic compound useful as such a microbicide is N-dodecyl morpholine (DDM). DDM is manufactured by BASF GmbH and by Buckman Laboratories International Inc., Memphis, Tenn.

Preferred N-alkyl heterocyclic compounds for use in the invention include N-dodecyl morpholine, N-dodecyl imidazole, N-dodecyl-2,6-dimethyl-morpholine, N-dodecyl-5-chloromethyl-2-oxazolidinone, N-dodecyl-2-pyrrolidinone, N-dodecyl hexamethyleneimine, N-dodecyl pyrrolidine, N-dodecyl-3-methyl-piperidine, N-dodecyl piperidine, N-dodecyl-4-methyl-piperidine, N-dodecyl-2-methyl-piperidine, 2-N-octylisothiazoline-3-one, and 4,5-dichloro-2-N-octyl-4-isothiazolin-3-one. Most preferred of these compounds are N-dodecyl morpholine, (DDM), and N-dodecyl imidazole, (DDI).

Any suitable triazole compound having microbicidal properties can be used as the second microbicide. A triazole compound or one of the salts or metal complexes thereof, can be:
A) 1-[2-(2,4-dichlorophenyl)-4-propyl-1,3-dioxolan-2-ylmethyl]-1H-1,2,4-triazole, commercial name propiconazole, (Reference: GB-1 522 657);
B) 1-{2-[2-chloro-4-(4-chlorophenoxy)-phenyl]-4-methyl-1,3-dioxolan-2-ylmethyl}-1H-1,2,4-triazole, commercial name difenoconazole, (Reference: GB-2 098 607);
C) α-[2-(4-chlorophenyl)ethyl]-α-(1,1-dimethylethyl)-1H-1,2,4-triazol-1-ethanol, commercial name tebuconazole, Reference: EP-A-40 345);
D) 1-(4-chlorophenoxy)-3,3-dimethyl-1-(1,2,4-triazol-1-yl)-butan-2-ol, commercial name triadimenol, (Reference: German Offenlegungsschrift 2 324 010);
E) 1-[3-(2-chlorophenyl)-2-(4-fluorophenyl)oxiran-2-ylmethyl]-1H-1,2,4-triazole, code name BAS-480-F, (Reference EP-A-196 038);
F) α-(4-chlorophenyl)-α-(1-cyclopropylethyl)-1H-1,2,4-triazol-1-ethanol, commercial name cyproconazole (Reference: U.S. Pat. No. 4,664,696);
G) 4-(4-chlorophenyl)-2-phenyl-2-(1,2,4-triazol-1-ylmethyl)-butyronitrile, proposed commercial name fenbuconazole (Reference: EP-A-251 775);
H) α-(2-fluorophenyl)-α-(4-fluorophenyl)-1H-1,2,4-triazol-1-ethanol, commercial name flutriafol (Reference: EP-A-15 756);
J) α-butyl-α-(2,4-dichlorophenyl)-1H-1,2,4-triazol-1-ethanol, commercial name hexaconazole (Reference: GB-2 119 653); or
K) 1-{[bis(4-fluorophenyl)methylsilyl]methyl}-1H-1,2,4-triazole, commercial name flusilazole (Reference: U.S. Pat. No. 4,510,136).

Propiconazole is described in U.S. Pat. Nos. 5,627,188, 5,567,705, 5,403,844, 5,326,777, 5,250,559 and 5,200,421, all incorporated by reference herein. Propiconazole has the following chemical structure:

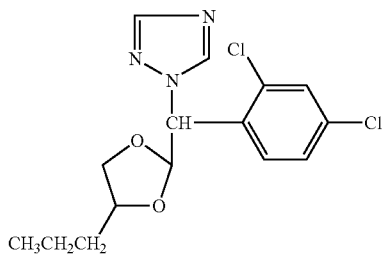

Propiconazole is also available under the BUSAN® 1292 tradename from Buckman Laboratories Inc., Memphis, Tenn. and under the WOCASEN 250EC tradename from Janssen Pharmaceutica, Titusville, N.J. BUSAN® 1292 is a formulation containing 23.6% propiconazole and 75% inert ingredients including a nonylphenol ethyleneoxide/polyethylene oxide surfactant.

Metal complexes can be composed of the organic molecule on which they are based and an inorganic or organic metal salt, for example the halides, nitrates, sulfates, phosphates, acetates, trifluoroacetates, trichloroacetates, propionates, tartrates, sulfonates, salicylates, benzoates, of the elements of the second main group such as calcium and magnesium and of the third and fourth main groups such as aluminium, tin or lead, and the first to eighth subgroups such as chromium, manganese, iron, cobalt, nickel, copper, or zinc. The metals can exist in the various valencies which they can assume. The metal complexes can be mono- or polynuclear, i.e. they can contain one or more organic moieties as ligands.

The triazole can exist in stereoisomeric forms or as racemates. While components C and G to J can form two stereoisomers, four stereoisomers are possible for each of the remaining components A (propiconazole), B (difenoconazole), D (triadimenol), E (BAS-480-F) and F (cyproconazole). The different isomeric forms of one of the preparations can differ in their biocidal activity. In the case of propiconazole, for example, the two cis isomers are preferred, i.e. those enantiomers in which the triazolylmethyl group and the propyl group are on the same side of the dioxolane ring. In the case of BAS-480-F, the two Z (=cis) enantiomers are preferred.

A microbicide with an activated halogen atom or a formaldehyde releasing compound can be used as the second microbicide. Examples are bronopol, chloroacetamide, and bronidox. Bronopol is also known as 2-bromo-2-nitropropane-1,3-diol. Bronopol is available as MYACIDE® from ANGUS Chemical Company, Northbrook Ill. The chemical formula of bronopol is:

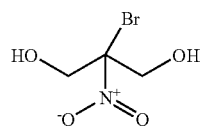

1,4-bis(bromoacetoxy)-2-butene (BBAB) can be used as the second microbicide in the present invention and can have the following formula:

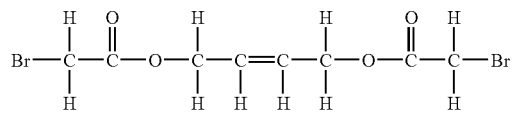

The synthesis of these compounds are described in U.S. Pat. No. 2,840,598, incorporated in its entirety by reference herein. The CAS No. for BBAB is 20679-58-7. BBAB has a molecular weight of 330 and is commercially available as a technical grade product from Bromine Compounds Ltd. In HPLC analysis, the technical grade of BBAB is about 87% BBAB, 4% 1-bromoacetoxy-4-dibromoacetoxy-2-butene (MBAB), and 4% of 1-bromoacetoxy-4-hydroxy-2-butene (BAFIB). All of these compounds are active ingredients and are considered microbicides. For purposes of the present invention, BBAB can include the presence of one or more of these other compounds in small quantities.

The boiling point of BBAB is about 135°-136° C. at 0.005 mm Hg, and the freezing point of BBAB is below −20° C. The solubility of BBAB in water is extremely low. BBAB is soluble in dimethylformamide and ethylene glycol monomethylether. BBAB is also soluble in an isopropanol, n-butanol, glycerol, ethylene glycol, propylene glycol, and diethylene glycol. The specific gravity of the technical grade of BBAB is 1.74 at 20° C.

Because BBAB has a high specific gravity, it has a higher density than water which adds to the problem that BBAB does not disperse well into aqueous systems such as water. In other words, BBAB can be considered water insoluble.

The emulsified concentrated formulation of the present invention contains at least BBAB as an active ingredient. The formulation can also contain a nonionic emulsifier that has a molecular weight range of from about 500 to about 8,000, preferably from about 800 to about 7,000 and more preferably from about 1,000 to about 6,000; and an HLB value of from about 7 to about 24, preferably from about 10 to about 20, and more preferably from about 13 to about 18. The formulation can contain an epoxidized oil, a hydrophilic solvent, and/or an anionic emulsifier.

The nonionic emulsifier is generally present in an amount from about 1 wt % to about 10 wt %, and preferably about 5 wt %. The BBAB formulation described in U.S. Pat. No. 5,681,581, incorporated by reference herein, can be used 2-(Thiocyanomethylthio)benzothiazole (TCMTB) can be used as the second microbicide. TCMTB is useful in controlling bacteria and fungi in various aqueous systems and is commercially available from Buckman Laboratories, Inc., Memphis, Tenn., under the tradenames BUSAN® 30WB and BUSAN® 1030 as a 30% active ingredient, and BUSANS® 30L product and BUSAN® 1118 product. The preparation and use of 2-(thiocyanomethyl-thio)-benzothiazole as a microbicide and a preservative is described in U.S. Pat. Nos. 3,520,976, 4,293,559, 4,866,081, 4,595,691, 4,944,892, 4,839,373, 5,073,638, and 4,479,961. U.S. Pat. No. 5,413,795 describes compositions having TCMTB adsorbed onto a solid carrier. The disclosures of all of these patents are incorporated herein by reference. TCMTB has the following chemical structure:

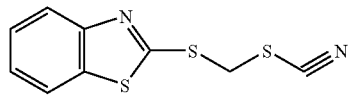

Methylene-bis(thiocyanate) (MTC) can be used as a second microbicide, and is described in U.S. Pat. No. 3,524,871, fully incorporated by reference herein. 2-(thiocyanomethylthio)benzothiazole and methylene-bis(thiocyanate) are both commercially available and they are also easily synthesized from commercially available raw materials. MTC is also known as 2-methylene-bis(thiocyanate).

The 2-(thiocyanomethylthio)benzothiazole and methylene-bis(thiocyanate) mixture is sold in varying concentrations under such commercial names as Busan® 1009, MECT, etc. These commercial products are available from Buckman Laboratories International, Inc. and other distributors, Busan® 1009 is an emulsifiable concentrate of 10% by weight of 2-(thiocyanomethylthio) benzothiazole and 10% by weight of methylene-bis(thiocyanate). The amounts of the active ingredients in the mixture used as a component in this invention can preferably vary from about 1% to about 80%, preferably from about 1% to about 40%, by weight of 2-(thiocyanomethylthio)benzothiazole and from about 1% to about 80%, preferably 1% to about 40%, by weight of methylene-bis(thiocyanate).

In accordance with the one or more compositions of the present invention, a halogenated acetophenone can be used as the second microbicide. The halogenated acetophenone is preferably a halogenated hydroxyacetophenone and more preferably has the formula:

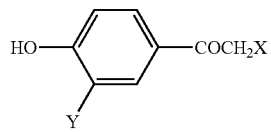

in which X is a halogen and Y is a halogen or H. Preferably X is Br, F, Cl or I and Y is H, Br, F, Cl or I. Most preferably, the halogenated acetophenone according to the present invention is 2-bromo-4'-hydroxyacetophenone. The preparation of monosubstituted 2-bromoacetophenones is described in U.S. Pat. No. 3,193,448, which disclosure is fully incorporated by reference. 2-bromo-4'-hydroxyacetophenone or BHAP is commercially available and is also easily synthesized from commercially available raw materials.

Suitable examples of halopropynyl compounds which may be used in the present invention include, but are not limited to, iodopropargyl derivatives including compounds derived from propargyl or iodopropargyl alcohols such as the esters, ethers, acetals, carbamates and carbonates and the iodopropargyl derivatives of pyrimidines, thiazolinones, tetrazoles, triazinones, sulfamides, benzothiazoles, ammonium salts, carboxamides, hydroxamates, and ureas. This class of compounds has the general formula:

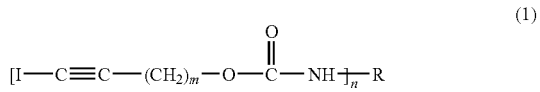

wherein R is selected from hydrogen, substituted and unsubstituted alkyl groups having from 1 to 20 carbon atoms, substituted and unsubstituted aryl, alkyl aryl, and aralkyl groups having from 6 to 20 carbon atoms and/or from substituted and unsubstituted cycloalkyl and cycloalkenyl groups of 3 to 10 carbon atoms, and m and n are independently integers from 1 to 3, i.e., m and n are not necessarily the same.

Preferred are formulations where m is 1 and n is 1 having the following formula:

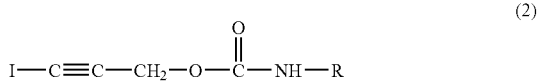

Suitable R substituents include alkyls such as methyl, ethyl, propyl, n-butyl, t-butyl, pentyl, hexyl, heptyl, octyl, nonyl, decyl, dodecyl, octadecyl, cycloalkyls such as cyclohexyl, aryls, alkaryls and aralkyls such as phenyl, benzyl, tolyl, cumyl, halogenated alkyls and aryls, such as chlorobutryl and chlorophenyl, and alkoxy aryls such as ethoxyphenyl and the like.

Compounds of this formula include iodopropargyl carbamates such as 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof. Most preferred is 3-iodo-2-propynyl butyl carbamate (IPBC).

IPBC is also known as iodopropargyl butyl carbamate. IPBC can be obtained from Troy Chemical, Newark, N.J. IPBC is disclosed in U.S. Pat. Nos. 3,923,870 and 5,219,875, incorporated by reference herein. IPBC has the following chemical formula:

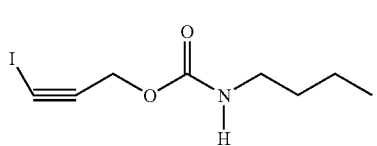

IPC is also known as Iodopropargyl carbamate. IPC, is disclosed in U.S. Pat. Nos. 4,945,109 and 5,328,926, incorporated by reference herein. The chemical formula of IPC is:

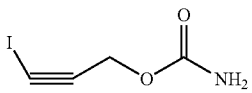

The composition can include one or more phenols as the second microbicide. Suitable phenols include alkyl, chloro, and nitro-substituted phenols and biphenols, and carboxylic acids thereof. Exemplary phenols include, but are not limited to phenol; 2,3-dimethylphenol; 3,5-dimethoxyphenol (3,5 DiMeOphenol); 2,6-dimethoxyphenol (2,6 DiMeOphenol); o-phenylphenol (OPP); p-tertiary-amylphenol (PTAP); o-benzyl-p-chlorophenol (OBPCP); para-chloro, meta-cresol (sold under the trade name PCMC by Howard Hall Div. R. W. Greeff and Co., Inc); o-cresol; p-cresol; 2,2-methylenebis(p-chlorophenol); 3,4-dihydroxybenzoic acid (3,4DiOH benzoic); p-hydroxybenzoic acid; caffeic acid; protocatechuic acid; p-nitrophenol; 3-phenylphenol; 2,3-dimethoxyphenol (2,3 DiMe-phenol); thymol; 4 chloro, 3-methoxyphenol; pentachlorophenol; hexachlorophene; p chloro-m-xylanol (PCMX); triclosan; 2,2-methoxy-bis(4-chloro-phenol); and para-phenylphenol.

Another class of second microbicides are iodosulfones, such as diidomethyl p-tolyl sulfone (CAS Reg, No. 20018-09-01), diiodomethyl p-chlorophenyl sulfone (CAS Reg. No. 20018-12-6) and the like, and mixtures thereof. These sulfones are known by their respective trademarks of AMICAL 48 and AMICAL 77; AMICAL FLOWABLE (EPA Reg. NO. 48301-24, from Angus Chem. Co.) is preferred. The AMICAL iodosulfones can be used, in general.

Halocyanoacetamide compounds can be used as the second microbicide and include, for example, 2,2-dibromo-3-nitrilopropionamide (DBNPA), 2-chloro-3-nitrilopropionamide-, 2-bromo-3-nitrilopropionamide, 2,2-dichloro-3-nitrilopropionamide and N-methyl-2,2-dibromo-3-nitrilopropionamide. Preferably the halocyanoacetamide compound is selected from one or more of DBNPA, 2,2-dichloro-3-nitrilopropionamide and N-methyl-2,2-dibromo-3-nitriloprop-ionamide; more preferably, the halocyanoacetamide is DBNPA. 2,2-dibromo-3-nitrilopropionamide (DBNPA) is described in U.S. Pat. No. 5,627,135, incorporated by reference herein.

Another class of a second microbicide is quaternary ammonium compounds. These include, but are not limited to, the following classes and examples of commercially available products: Monoalkyltrimethyl ammonium salts (Examples of commercially available products include cetyltrimethylammonium bromide or chloride as CTAB, tetradecyltrimethylammonium bromide or chloride (TTA), alkyltrimethyl ammonium chloride, alkylaryltrimethyl ammonium chloride, dodecyltrimethylammonium bromide or chloride, dodecyldimethyl-2-phenoxyethylammonium bromide, hexadecylamine: chloride or bromide salt, dodecyl amine or chloride salt, and cetyldimethylethyl ammonium bromide or chloride.), Monoalkyldimethylbenzyl ammonium salts (Examples include alkyldimethylbenzyl ammonium chlorides and benzethonium chloride as BTC), Dialkyldimethyl ammonium salts (Commercial products include domiphen bromide as DB, didecyldimethyl ammonium halides, and octyldodecyldimethyl ammonium chloride or bromide.), Heteroaromatic ammonium salts (Commercial products include cetylpyridium halides (CPC or bromide salt and hexadecylpyridinium bromide or chloride), cis-isomer 1-[3-chloroallyl]-3,5,7-triaza-1-azoniaadamantane, alkylisoquinolinium bromide, and alkyldimethylnaphthylmethyl ammonium chloride (BTC 1110). Polysubstituted quaternary ammonium salts, (Commercially available products include, but are not limited to alkyldimethylbenzyl ammonium saccharinate and alkyldimethylethylbenzyl ammonium cyclohexylsulfamate), Bis-quaternary ammonium salts (Product examples include 1,10-bis(2-methyl-4-aminoquinolinium chloride)-decane, 1,6-Bis {1-methyl-3-(2,2,6-trimethyl cyclohexyl)-propyldimethyl ammonium chloride]hexane or triclobisonium chloride, and the bis-quat referred to as CDQ by Buckman Brochures), and polymeric quaternary ammonium salts (includes polyionenes such as poly[oxyethylene (dimethyliminio)ethylene(di-methyliminio)ethylene dichloride], poly[N-3-dimethylammonio)propyl]N-[3-ethylneoxyethylenedimethylammonio)propyl]urea dichloride, and alpha-4-[1-tris(2-hydroxyethyle)ammonium chloride).

Further, examples of second microbicides which may be present according to the invention are isothiazolones, such as N-octylisothiazolone (e.g. Kathon 893=45% N-octylisothiazolone in 1,2-propylene glycol), 5-chloro-N-methylisothiazolone and N-methylisothiazolone (e.g. Kathon 886=salt-containing mixture of 5-chloro-N-methylisothiazolone and N-methylisothiazolone), benzisothiazolone, 4,5-dichloro-N-octylisothiazolone, Promexal, N-butyl-BIT and others, aldehydes or aldehyde donor compounds, such as, for example, formaldehyde, glutaraldehyde, o-phthalaldehyde, ethylene glycol bishemiformal, propylene glycol hemiformal, butyl glycol hemiformal, diethylene glycol butyl ether hemifornal, benzyl alcohol hemiformal, Grotan Bk, Mar 71, Grotan W S, dimethyldimethylolhydantoin (DMDMH), Protectol 140, dimethylolurea, N-methylolchloroacetamide, Dowicil 200, sodium hydroxymethylglycinate, organohalogen compounds, such as IPBC, dibromo-dicyanobutane (DBDCB), chloroacetamide, Bronopol, Amical 48, trichlorocarbanilide, sulphur-containing compounds, such as 2-mercapto-pyridine N-oxide and salts thereof (e.g. Pyrion-Na) or complex compounds (e.g. zinc pyrithione), pyrion disulphide, TCMTB, Preventol VPOC 3061, tetramethylthiuram disulphide, 3,5-dimethylthiadiazinethione, methylene bisthiocyanate, thiabendazole, active oxygen compounds, such as t-butyl hydroperoxide, phenols and salts thereof, such as p-chloro-m-cresol, p-chloro-m-xylenol, o-phenylphenol, o-benzyl-4-chlorophenol, parabens, Irgasan DP 300, algicides, such as Diuron, Terbutyn, Prometryn, Irgarol 1051, N-cyclohexyl-diazenium dioxide or salts or complexes, such as the K salt, Al complex, Lonzabac 12 and others, cation-active ingredients, such as benzalkonium chloride (solid and 50% strength aqueous solution), cetylpyridinium salts, dodecylguanidine or salts thereof, chlorhexidine salts, octenidine salts, laurylpropylenediaminequanidinium acetate, Vantocil IB and others.

Additional examples of second microbicides include formaldehyde (HCHO) or a formaldehyde-releasing substance, 2-bromo-2-nitro-1,3-propanediol (bronopol, BNP), polyhexamethylenebiguanide (PMG), o-phenylphenol (OPP), a pyrithione, preferably zinc pyrithione (ZnPy), sodium pyrithione (NaPy), copper pyrithione (CuPy) and iron pyrithione (FePy), N-butyl-1,2-benzoisothiazol-in-3-one (BBIT), N-hydroxymethyl-1,2-benzoisothiazolin-3-one (HMBIT) and/or a benzalkonium chloride, preferably dimethylbenzylalkonium chloride (BAC).

Further examples of second microbicides that may be used in the present invention include isothiazolone, derivatives thereof, compounds having isothiazolone functions, 3-isothiazolone, 5-chloro-2-methyl-3-isothiazolone, 1-methyl-3,5,7-triaza-1-azoniatricyclo (3.3.1.1) decane chloride, 4,5-dichloro-2-octyl-3 isothiazolone, 2-bromo-2-nitropropanediol, 5-bromo-5-nitro dioxane, thiocyanomethylthiobenzothiazole, 4,5-dichloro-2-octyl-3-isothiazolone and 2n-octyl-3-isothiazolone, tetrachloroisophalonitrile, 1,2-benzisothiazolin-3-one, 2-methyl-4,5-trimethylene-4-isothiazolin-3-one, 5-chloro-2-methyl-4 isothiazolin-3-one, 2-methyl-4-isothiazolin-3-one, 4-(2-nitrobutyl)morpholine, beta-nitrostyrene ("NS"), beta-bromo-beta-nitrostyrene ("BNS"), methylchlorolisothiazolone ("IZN"), methylenebisthiocyanate ("MBT"), 2,2dibromo-3-nitrilopropionamide ("DBNPA"), 2-bromo-2-bromomethyl-glutaronitrile ("BBMGN"), alkyldimethylbenzylammonium chloride ("ADBAC"), and beta-nitrovinyl furan ("NVF"), 2-methyl-3-isothiazolone, methylene bisthiocyanate, p-tolyldiiodomethyl sulfone, 2-methylthio-4-tertbutylamino-6-cyclopropyl-amino-s-triazine, N,N-dimethyl-N'-phenyl-(N'fluorodichloromethylthio)sulfa-inide, sulfamides, tetracycline, isothiazolone derivatives, N-(cyclo)alkyl-isothiazolone, benzisothiazolin-3-one, and mixtures of the foregoing.

The microbicides in the composition of this invention may be used "as is" or may first be formulated with a solvent or a solid carrier. Suitable solvents include, for example, water; glycols, such as ethylene glycol, propylene glycol, diethylene glycol, dipropylene glycol, polyethylene glycol, and polypropylene glycol; glycol ethers; alcohols, such as methanol, ethanol, propanol, phenethyl alcohol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; and mixtures thereof. It is preferred that the solvent is selected from water, glycols, glycol ethers, esters and mixtures thereof. Suitable solid carriers include, for example, cyclodextrin, silicas, diatomaceous earth, waxes, cellulosic materials, alkali and alkaline earth (e.g., sodium, magnesium, potassium) metal salts (e.g., chloride, nitrate, bromide, sulfate) and charcoal.

A microbicide component also can be formulated in the form of a dispersion. The solvent component of the dispersion can be an organic solvent or water, preferably water. Such dispersions can contain adjuvants, for example, co-solvents, thickeners, anti-freeze agents, dispersants, fillers, pigments, surfactants, biodispersants, sulfosuccinates, terpenes, furanones, polycations, stabilizers, scale inhibitors and anti-corrosion additives.

When a microbicide component is formulated in a solvent, the formulation may optionally contain surfactants. When such formulations contain surfactants, they are generally in the form of emulsive concentrates, emulsions, microemulsive concentrates, or microemulsions. Emulsive concentrates form emulsions upon the addition of a sufficient amount of water. Microemulsive concentrates form microemulsions upon the addition of a sufficient amount of water. Such emulsive and microemulsive concentrates are generally well known in the art; it is preferred that such formulations are free of surfactants. U.S. Pat. No. 5,444,078 may be consulted for further general and specific details on the preparation of various microemulsions and microemulsive concentrates.

As described above, components (a) cyanodithiocarbimate and (b) the second microbicide can be used in a synergistically effective amounts. The weight ratios of (a) to (b) vary depending on the type of microorganisms and product, material, or media to which the composition is applied. In view of the present invention, one skilled in the art can readily determine, without undue experimentation, the appropriate weight ratios for a specific application. The ratio of component (a) to component (b) preferably ranges from 1:99 to 99:1, more preferably from 1:30 to 30:1, and most preferably 1:2 to 2:1.

Depending upon the specific application, the composition can be prepared in liquid form by dissolving the composition in water or in an organic solvent, or in dry form by adsorbing onto a suitable vehicle, or compounding into a tablet form. The preservative containing the composition of the present invention may be prepared in an emulsion form by emulsifying it in water, or if necessary, by adding a surfactant. Additional chemicals, such as insecticides, may be added to the foregoing preparations depending upon the intended use of the preparation.

The mode as well as the rates of application of the composition of this invention could vary depending upon the intended use. The composition could be applied by spraying or brushing onto the material or product. The material or product in question could also be treated by dipping in a suitable formulation of the composition. In a liquid or liquid-like medium, the composition could be added into the medium by pouring, or by metering with a suitable device so that a solution or a dispersion of the composition can be produced.

The synergistic activity of the combinations described above has been confirmed using standard laboratory techniques as illustrated below. The following examples are intended to illustrate, not limit, the present invention.

Microbicidal Evaluation

Fungal Evaluation

Mineral salts-glucose medium was used. To prepare the medium, the following ingredients were added to 1 liter of deionized water: 0.7 g of $KH_2PO_4$; 0.7 g of $MgSO_4 \cdot 7H_2O$; 1.0 g of $HN_4NO_3$; 0.005 g of NaCl; 0.002 g of $FeSO_4 \cdot 7H_2O$; 0.002 g $ZnSO_4 \cdot 7H_2O$; 0.001 g of $MnSO_4 \cdot 7H_2O$; 10 g of Glucose. The pH of the medium was adjusted to 6 with 1N NaOH. The medium was distributed in 5 ml amounts in test tubes and autoclaved at 121° C. for 20 minutes. The fungus, *Aspergillus niger*, was grown on potato dextrose agar slant for 5 to 10 days and a spore suspension prepared by washing down the spores from the slant into a sterile saline solution. After addition of the biocides in the desired concentrations in the sterile mineral salts-glucose medium, the fungal spore suspension was added. The final spore concentration was approximately $10^6$ cfu/ml. The inoculated media was incubated at 25° C. for 7 days. The experimental design is termed a "factual experiment" in which each test concentration of compound A is combined with each test concentration of compound B.

In the following examples, synergism was demonstrated in separate experiments by testing combinations of the a) cyanodithiocarbimate (designated component A), and b) an N-alkyl heterocyclic compound; a triazole compound or salt thereof or metal complex thereof; a microbicide with an activated halogen atom or a formaldehyde releasing compound; 1,4-bis(bromoacetoxy)-2-butene; 2-(thiocyanomethylthio) benzothiazole; a methylene-bis(thiocyanate); a halogenated acetophenone; a halopropynl compound; an iodosulfone; a phenol; a halocyanoacetamide compound; or a quaternary ammonium compound (designated component B) in a series of tests in varying ratios and a range of concentrations against the fungus *Aspergillus niger*.

The lowest concentration of each mixture or compound which completely prevented growth of the fungus for seven days was taken as the end point for synergism calculations. End points for the various mixtures were then compared with the end points for the pure active ingredients alone in concomitantly prepared flasks or test tubes.

Synergism was demonstrated by the method described by Kull, E. C., et al., APPLIED MICROBIOLOGY 9:538-541 (1961):

QA/Qa+QB/Qb wherein
Qa=Concentration of compound A in parts per million, acting alone, which produced an end point.
Qb=Lowest concentration of compound B in parts per million, acting alone, which produced an end point.
QA=Lowest concentration of compound A in parts per million, in the mixture, which produced an end point.
QB=Lowest concentration of compound B in parts per million, in the mixture, which produced an end point.

When the sum of QA/Qa and QB/Qb is greater than one, antagonism is indicated. When the sum is equal to one, additivity is indicated. When the sum is less than one, synergism exists.

This procedure for demonstrating synergism of the compositions of this invention is a widely used and acceptable procedure. More detailed information is provided in the article by Kull et al. Further information concerning this procedure is contained in U.S. Pat. No. 3,231,509, the disclosure of which is herein incorporated in its entirety by reference.

Based on the above criteria, a synergistic activity against fungi is observed when an cyanodithiocarbimate is combined with the identified second microbicides. Examples showing synergistic results can be found in the table below.

In general, an effective fungicidal, bactericidal, or algicidal response can be obtained when the synergistic combination is employed in concentrations ranging about 0.01 ppm to 1% (i.e., 10,000 ppm) of the cyanodithiocarbimate, preferably 0.1 to 5,000 ppm, and most preferably 0.1 ppm to 1000 ppm; and from about 0.01 to 5,000 ppm of the second microbicide, preferably 0.1 to 3,000 ppm, and most preferably, 0.1 to 1,000 ppm.

This study examined the interaction between the S-chloromethyl-S'-hexylcyanodithioimidocarbimate and a second microbicide selected from TCMTB, MTC, BHAP, DDM (BUSPERSE® 2180 microbicide), BUSAN® 1144 microbicide (Bromopol), BUSAN® 1210 microbicide (BBAB), IPBC, propiconazole, 4,5-dichloro-2-N-octyl-4-isothiazolin-3-one, 2-N-octyl-4-isothiazolin-3-one, BUSAN® 1014 microbicide (CDQ), BUSAN® 94 microbicide (DBNPA), Preventol WB (PCMC+OPP), and Amical.

For: X<1 A and B are synergistic
X=1 A and B are additive
X>1 A and B are antagonistic For combinations of cyanodithiocarbimate with the selected second microbicide, the calculated values of X in each case are:

| Second Microbicide | Test 1 | Test 2 | Test 3 |
|---|---|---|---|
| TCMTB | 0.27 | 0.25 | 0.7 |
| MTC | 0.64 | 0.46 | 0.29 |
| BHAP | 1.22 | 1.0 | 0.8 |
| BUSPERSE 2180 | 0.62 | 0.74 | — |
| IPBC | 0.86 | 0.3 | — |
| Propiconazole | — | — | 0.34 |

-continued

| Second Microbicide | Test 1 | Test 2 | Test 3 |
|---|---|---|---|
| 4,5,-dichloro-2-N-octyl-4-isothiazolin-3-one | 0.7 | 0.5 | — |
| 2-N-octyl-4-isothiazolin-3-one | 0.64 | — | — |
| BUSAN 1014 | 0.27 | 0.31 | ≦0.53 |
| PREVENTOL WB | <0.84 | ≦0.22 | ≦0.21 |
| AMICAL | 0.34 | 0.65 | 1.03 |
| BUSAN 1144 | 0.69 | 0.57 | — |
| BUSAN 1210 | 0.59 | 0.61 | — |

Examples of Observed Q Values Used in the Calculation of a Synergy Ratio

Compound A=S-Hexyl-S'-chloromethylcyanodithiocarbimate
Q=ppm active ingredient

| Compound B | $Q_A$ | $Q_a$ | $Q_B$ | $Q_b$ |
|---|---|---|---|---|
| TCMTB | 0.15 | 0.35 | 0.05 | 1.0 |
| MTC | 0.05 | 0.35 | 0.1 | >0.7 |
| BHAP | 0.3 | 0.2 | 1.0 | >8.0 |
| Bsp 2180 | 0.05 | 0.3 | 20.0 | >140.0 |
| IPBC | 0.025 | 0.25 | 0.05 | 0.35 |
| Propiconazole | 0.175 | 0.175 | 0.025 | 0.2 |
| 4,5-Dichloro-2-N-octyliso-Thiazolinone | 0.05 | 0.25 | 0.1 | 0.2 |
| 2-N-octylisothiaz-Olinone | 0.1 | 0.3 | 0.025 | >0.175 |
| Busan 1014 | 0.1 | 0.3 | 10.0 | 40.0 |
| Preventol WB | 0.15 | 0.25 | 20.0 | >140.0 |
| Amical | 0.025 | 0.175 | 0.05 | 0.1 |
| Busan 1144 | 0.2 | 0.3 | 50.0 | >550.0 |
| Busan 1210 | 0.05 | 0.3 | 0.25 | >2.75 |

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention will be limited to the specific values recited when defining a range.

Other embodiments of the present invention will be apparent to those skilled in the art from consideration of the specification and practice of the invention disclosed herein. It is intended that the specification and examples be considered exemplary only, with a true scope and spirit of the invention being indicated by the following claims.

What is claimed is:

1. A composition comprising (a) cyanodithiocarbimate and (b) at least one second microbicide selected from 1,4-bis (bromoacetoxy)-2-butene; 2-(thiocyanomethylthio)benzothiazole; a methylene-bis(thiocyanate); 2-bromo-4'-hydroxyacetophenone; N-dodecyl morpholine; iodopropargyl butyl carbamate; propiconazole; 4,5-dichloro-2-N-octyl-4-isothiazolin-3-one; 2-N-octyl-4-isothiazolin-3-one; bis-quat of triclobisonium chloride; meta-cresol; o-phenylphenol; diiodomethyl p-tolyl sulfone; diiodomethyl p-chlorophenyl sulfone; or bromopol, and said cyanodithiocarbimate has the formula

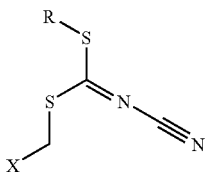

where X is a chloro and R is a $C_1$-$C_{14}$ alkyl group, wherein components (a) and (b) are present in a synergistically microbicidally effective combined amount to control the growth of at least one microorganism.

2. The composition of claim 1, wherein (a) to (b) are present at a weight ratio of from about 1:30 to about 30:1.

3. The composition of claim 1, wherein (a) to (b) are present at a weight ratio of from about 1:2 to about 2:1.

4. The composition of claim 1, wherein (b) is 1,4-bis(bromoacetoxy)-2-butene.

5. The composition of claim 1, wherein (b) is 2-(thiocyanomethylthio)benzothiazole.

6. The composition of claim 1, wherein (b) is a methylene-bis(thiocyanate).

7. The composition of claim 1, wherein (b) is 2-bromo-4'-hydroxyacetophenone.

8. The composition of claim 1, wherein (b) is N-dodecyl morpholine.

9. The composition of claim 1, wherein (b) is iodopropargyl butyl carbamate.

10. The composition of claim 1, wherein (b) is propiconazole.

11. The composition of claim 1, wherein (b) is 4,5-dichloro-2-N-octyl-4-isothiazolin-3-one.

12. The composition of claim 1, wherein (b) is 2-N-octyl-4-isothiazolin-3-one.

13. The composition of claim 1, wherein (b) is bis-quat of triclobisonium chloride.

14. The composition of claim 1, wherein (b) is meta-cresol.

15. The composition of claim 1, wherein (b) is o-phenylphenol.

16. The composition of claim 1, wherein (b) is diiodomethyl p-tolyl sulfone.

17. The composition of claim 1, wherein (b) is diiodomethyl p-chlorophenyl sulfone.

18. The composition of claim 1, wherein (b) is bromopol.

19. The composition of claim 1, where R is a $C_6$ alkyl group.

20. A method of controlling the growth of at least one microorganism in or on a product, material, or medium susceptible to attack by a microorganism, the method comprising adding to the product, material, or medium the composition of claim 1.

21. The method of claim 20, wherein the microorganism is a fungus.

22. The method of claim 20, wherein the material or medium is wood pulp, wood chips, lumber, paints, leathers, adhesives, coatings, animal hides, tanning liquor, paper mill liquor, metalworking fluids, petrochemicals, pharmaceutical formulations, cooling water, recreational water, dyes, clays, mineral slurries, cationic surfactants, formulations with cationic surfactants, influent water, waste water, pasteurizers, retort cookers, cosmetic formulations, toiletry formulations, textiles, geological, drilling lubricants, or agrochemical compositions for crop or seed protection.

23. The method of claim 20, wherein the material or medium is in the form of a solid, a dispersion, an emulsion, or a solution.

24. A method for controlling spoilage of a product, material, or medium caused by microorganism selected from bacteria, fungi, algae, or mixtures thereof, wherein the method comprises adding to the product, material, or medium a composition of claim 1.

25. The method of claim 24, wherein the material is seeds or crops.

* * * * *